United States Patent [19]

Peterson

[11] 4,055,413
[45] Oct. 25, 1977

[54] NOVEL ORGANOTIN HERBICIDAL COMPOUNDS

[75] Inventor: Donald J. Peterson, Cincinnati, Ohio

[73] Assignee: The Procter & Gamble Company, Cincinnati, Ohio

[21] Appl. No.: 322,328

[22] Filed: Jan. 10, 1973

Related U.S. Application Data

[62] Division of Ser. No. 23,457, March 27, 1970, Pat. No. 3,725,446.

[51] Int. Cl.$^2$ ............................................. A01N 9/12
[52] U.S. Cl. .......................................... 71/97; 71/76; 424/288
[58] Field of Search ............................................. 71/97

[56] References Cited

U.S. PATENT DOCUMENTS 3,499,086  3/1970  Bruckner et al. .................... 71/97 X

FOREIGN PATENT DOCUMENTS 4413-69  2/1969  Japan ........................................ 71/97

Primary Examiner—Lewis Gotts
Assistant Examiner—Catherine L. Mills
Attorney, Agent, or Firm—Rose Ann Dabek; L. G. Xiarhos; R. C. Witte

[57] ABSTRACT

Disclosed are novel organotin compounds and a process for preparing same. These organotin compounds correspond to the general formula:

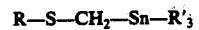

where R is alkyl of from 1 to 14 carbon atoms; aryl; or substituted aryl; and each R' is alkyl of 1 to 14 carbon atoms. The organotin compounds of the invention having pre-emergent and post-emergent herbicidal activity are employed in the formulation of herbicidal compositions effective for controlling or combating the growth of weeds and other undesirable vegetation.

4 Claims, No Drawings

NOVEL ORGANOTIN HERBICIDAL COMPOUNDS

This is a division of application Ser. No. 23,457, filed Mar. 27, 1970, now U.S. Pat No. 3,725,446.

BACKGROUND OF THE INVENTION

This invention relates to novel compounds. More particularly, this invention relates to organotin compounds, a method for their preparation, herbicidal compositions containing such compounds and to a method of controlling the growth of weeds and other undesirable vegetation.

The undesirability of a mixed growth of weed plants and crop plants is universally acknowledged. Such weed plants, including the monocotyledonous and dicotyledonous weeds such as mustard, pigweed, crabgrass, and foxtail, are undesirable from the standpoint of competing with commercial crops for vital soil nutrients. The result is frequently the harvesting of lower yields and poorer crops than might otherwise be obtained.

While it has been possible to control weed growth by mechanical means, with the aid of horse- or tractor-drawn cultivators, such efforts are time-consuming laborious tasks. More recently, it has been possible to control weed growth by the periodic application of biologically-active compounds having pre-emergent and/or post-emergent activity.

It is an object of the present invention to provide novel organotin compounds and a method for their preparation.

A further object of the present invention is to provide novel compounds which are useful as pre-emergent and post-emergent herbicides.

Another object is to provide herbicidal compositions containing the novel organotin compounds of the invention.

A still further object is to provide a method of controlling the growth of weeds and other undesirable vegetation.

Other objects of the invention will be apparent from consideration of the invention described more fully hereinafter.

DESCRIPTION OF THE INVENTION

The novel organotin compounds of the present invention have the formula:

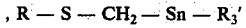

where R is a member selected from the group consisting of alkyl of from 1 to 14 carbon atoms (e.g., methyl, ethyl, n-propyl, iso-propyl, n-butyl, iso-butyl, amyl, iso-amyl, n-hexyl, n-octyl, n-dodecyl, n-tetradecyl); aryl (e.g., phenyl, naphthyl); substituted-aryl (e.g., p-methoxyphenyl, p-N,N-dimethylaminophenyl, o-methoxyphenyl); and each R' is alkyl of from 1 to 14 carbon atoms.

In a process aspect this invention comprises reacting an organometallic compound having the formula:

wherein M is alkali metal (e.g., sodium, potassium, lithium) with a trialkyltin halide of the formula $R_3'SnX$ wherein R and each R' are as defined hereinbefore and X is halide (e.g., chloride, bromide). The reaction of the organometallic compound and trialkyltin halide proceeds with facility according to the following scheme:

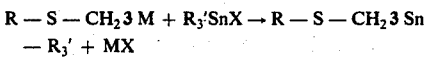

Organometallic reactants suitable for reaction with a trialkyltin halide according to the process of the invention include the (alkylthio)methyllithiums; (arylthio)methyllithiums; and (substituted-arylthio)methyllithiums. Specific examples include (methylthio)methyllithium; (butylthio)methyllithium; (n-decylthio)methyllithium; (n-tetradecylthio)methyllithium; (phenylthio)methyllithium; (p-methoxyphenylthio)methyllithium; and (o-methoxyphenylthio)methyllithium.

The process of the present invention is carried out at a temperature of from about $-60°$ C to about $30°$ C, a preferred temperature being from $-10°$ C. Especially suitable herein are proportions of reactants corresponding to about stoichiometric amounts. Examples of suitable trialkyltin halides for reaction with the organometallic reactants hereinbefore described include trimethyltin chloride, triethyltin chloride, tri-n-propyltin chloride, tri-iso-propyltin chloride, tri-n-butyltin chloride, tri-iso-butyltin chloride, triamyltin chloride, tri-iso-amyltin chloride, tri-n-hexyltin chloride, tri-n-octyltin chloride, tri-n-decyltin chloride, tri-n-dodecyltin chloride, trimethyltin bromide, tri-n-tetradecyltin chloride, tri-n-butyltin bromide and the like.

Tri-n-butyltin chloride is a preferred trialkyltin halide herein and undergoes the desired reaction with facility. Its ready availability and reaction with (methylthio)methyllithium, for example, to provide (methylthiomethyl)tributyltin having unique pre-emergent herbicidal properties make the tributyltin chloride the trialkyltin halide reactant of choice.

The process of the present invention can be conducted in the presence of non-reactive solvents or diluents. These solvents or diluents should not contain any of the reactive groups contained in the reactive compounds hereinbefore mentioned either as a part of the structure of the solvent or as part of impurities present in the solvents if maximum yields are desired. The use of solvents which will react with organolithium reactants is also generally undesirable. Suitable non-reactive solvents or diluents are to be found in such classes of compounds as the aliphatic hydrocarbons, aliphatic ethers, cyclic ethers and trialkylamines. Examples of suitable non-reactive hydrocarbon solvents include hexane, petroleum ether and "Stoddard" solvent. Among the ether compounds which are suitable as solvents are diethyl ether, dibutyl ether, tetrahydrofuran, 1,2-dimethoxyethane and diethylene glycol dimethyl ether. Amine compounds which can serve as solvents for the reaction include triethylamine and N,N,N',N'-tetramethylethylenediamine. Other similar non-reactive solvents or diluents can be used with substantially equivalent results. Preferred herein are diethyl ether and tetrahydrofuran which enable formation of the desired products in high yield and degree of purity. The use of mixtures of two or more non-reactive compounds as the reaction medium is suitable.

The organometallic, e.g., organolithium reactants described hereinbefore, can be readily prepared. Generally, these reactants can be prepared by reaction of a methyl sulfide having the formula:

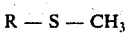

wherein R is as hereinbefore defined with a metalating agent such as alkali metal alkyls, wherein the alkyl group contains from 1 to about 6 carbon atoms; and alkali metal aryls. Preferred metalating agents include n-butyllithium from the standpoints of facility of reaction and ready availability. An especially preferred metalating agent is a complex of an alkyllithium, hereinbefore defined, and an amino compound having the formula $(R^2)_2N\ R^3N(R^2)_2$ wherein each $R^2$ is alkyl of from 1 to about 20 carbon atoms and $R^3$ is a saturated alkylene group of from 1 to 5 carbon atoms and wherein the total number of carbon atoms in such amino compound is from 5 to 20. A preferred complex is a 1:1 mole ratio complex of tri-n-butyllithium and N,N,N', N'-tetramethylethylenediamine.

The organometallic reactants of the process of the invention are conveniently prepared by reaction with an appropriate metalating agent at a temperature of from $-60°$ C to about 100° C depending on the particular sulfide, metalating agent, solvent and the like. Reactions of methylsulfides with n-butyllithium occur rapidly at room temperature. Aliphatic hydrocarbon solvents, e.g., hexane, are preferred when the alkali metal alkyl-amine complexes are employed. Aliphatic and cyclic ethers should be employed where the alkyllithium compounds are employed for metalation.

Metalation of the sulfides with n-butyllithium, for example, proceeds according to the following scheme:

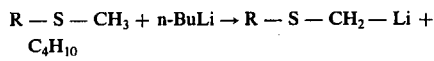

Preparations of organolithium reactants of the process of the invention are described in greater detail by Peterson, *J. Org. Chem.*, 32, 1717, (1967); by Corey and Seebach, *J. Org. Chem.*, 31, 4097 (1966); by Gilman and Webb, *J. Am. Chem. Soc.*, 62, 987 (1940); and in applicant's copending U.S. Pat. No. 3,502,731, issued Mar. 24, 1970, incorporated by reference thereto.

The products and process of the present invention are described in more detail in the following Examples.

EXAMPLE I

PART A. PREPARATION OF (METHYLTHIO)METHYLLITHIUM 250-ml, three-necked flask fitted with a stirrer, a dropping funnel, and a thermometer was swept thoroughly with argon and maintained in an air-free condition by a mercury-filled trap. 5.8 gm. (0.05 mole) of N,N,N', -tetramethylethylenediamine (TMEDA) was added to 36 ml. of 1.4 molar (0.05) n-butyllithium in hexane to form 0.05 mole of the n-butyllithium-TMEDA complex. (The temperature in these reactions was held below about 20° C. by means of a water bath.) 3.1 g. (0.05 mole) of dimethyl sulfide was added to the complex and after about a quarter of an hour a white precipitate had formed. This precipitate was composed of lithium melthyl mercaptide and (methylthio) methyllithium. After about four hours, the resulting reaction mixture containing the (methylthio)methyllithium (MTML) was used in the following reaction.

When in the above example the following alkyl methyl sulfides, aryl methyl sulfides and substituted-aryl methyl sulfides are substituted on a molar basis for the dimethyl sulfide, substantially equivalent results are obtained in that the corresponding (alkylthio)methyllithium, (arylthio)methyllithium and (substituted-arylthio)methyllithium compounds are prepared: methyl, ethyl, n-propyl, isopropyl, n-pentyl, isopentyl, n-hexyl, 2,2-dimethylpentyl, n-heptyl, n-octyl, 2,2-dimethylhexyl, isooctyl, 2-ethylhexyl, n-nonyl, n-decyl, tripropylene, undecyl, n-dodecyl, tetrapropylene, tridecyl, n-tetradecyl, biphenyl, naphthyl, 4-methyldecyl, 4-decyl, p-methoxyphenyl, o-methoxyphenyl and p-N,N-dimethylaminophenyl methyl sulfides.

When in the above example the following metalating agents are substituted on a molar basis for n-butyllithium-TMEDA complex substantially equivalent results are obtained in that the (alkylthio)methylmetal compounds are prepared: phenylsodium; phenylpotassium; methyl, ethyl, propyl, butyl, pentyl and hexyl sodiums and potassiums; the complexes of methyl, ethyl, propyl, butyl, pentyl, octyl, decyl, tetrapropylene, hexadecyl, dodecyl, octadecyl and eicosyl lithiums with N-methyl, N-ethyl, N'-propyl, N'-butylpropylenediamine, N-dodecyl, N,N',N'-trimethylmethylenediamine, N-octyl, N,N',N'-triethylbutylenediamine, N,N,N',N'-tetraethylpropylenediamine, or N-eicosyl, N,N',N'-trimethylethylenediamine.

When in the above example of the following saturated hydrocarbons are substituted, either wholly or in part (e.g., 1:1 mixtures), for the hexane, substantially equivalent results are obtained in that the (alkylthio)methylmetal compounds are prepared: pentane, octane, isooctane, nonane, decane, isododecane, and cyclophexane.

PART B: REACTION OF THE TRIBUTYLTIN CHLORIDE WITH (METHYLTHIO)METHYLLITHIUM

Fifty mls. of a one-molar solution of (methylthio) methyllithium TMEDA complex (0.05 mole) in hexane, obtained as described in Part A, was added dropwise over a period of one-quarter hour to a solution of 16.3 g. (0.05 mole) of tributyltin chloride in 50 ml. of diethyl ether. The mixture was stirred for an additional one-hour period and the reaction mixture was carefully hydrolyzed with 50 ml. of one-molar ammonium chloride. The organic layer was dried over sodium sulfate, concentrated and distilled under reduced pressure to give 14 g. of (methylthiomethyl)tributyltin, bp 107° C. (0.07 mm.). Infrared and proton nuclear magnetic resonance spectral analyses confirmed the assigned structure.

When in Part B above the following trialkyltin halides are substituted on a molar basis for the tributyltin chloride, substantially equivalent results are obtained in that the corresponding (methylthiomethyl)trialkyltins are prepared: trimethyltin chloride; triethyltin chloride; tri-n-propyltin chlorides; tri-iso-propyltin; tri-n-pentyltin chloride; tri-n-hexyltin chloride; tri-n-octyltin chloride; tri-n-decyltin chloride; tri-n-dodecyltin chloride; tri-n-tetradecyltin chloride; trimethyltin bromide; tributyltin bromide; tri-n-dodecyltin bromide and tri-n-tetradecyltin bromide.

EXAMPLE II

Using the apparatus and procedure of Example I, 100 ml. of an approximately one-molar solution of (phenylthio) methyllithium in hexane-THF solvent was added dropwise with stirring to 0.1 mole of tributyltin chloride dissolved in THF. The temperature was maintained by means of an ice bath in the range of from 0° C to 20 C. Following the complete addition over a one-half hour period, the reaction mixture was stirred for 1.5 hours at room temperature and hydrolyzed by pouring into aqueous one-molar ammonium chloride. Extraction from the hydrolyzate with ether solvent and purification by vacuum distillation yielded the desired product, (phenylthiomethyl) tributyltin, b.p. 152°–157° C (0.09 mm). Infrared and proton nuclear magnetic resonance spectral analyses confirmed the assigned structure.

EXAMPLE III

Using the apparatus and procedure of Example I, 100 ml. of an approximately one-molar solution of (p-methoxyphenylthio)methyllithium in hexane-THF solvent is added dropwise with stirring to 0.1 mole of tributyltin chloride dissolved in THF. The temperature is maintained by means of an ice bath in the range of from 0° C to 10° C. Following the complete addition over a one-quarter hour period, the reaction mixture is stirred for two hours at room temperature and hydrolyzed by pouring into aqueous one-molar ammonium chloride. Extraction from the hydrolyzate with ether solvent and purification by vacuum distillation yields the desired product, (p-methoxyphenylthiomethyl)-tributyltin.

EXAMPLE IV

The compound of Example I, (methylthiomethyl)-tributyltin, was evaluated for pre-emergent and post-emergent herbicidal activity employing the methods described in greater detail hereinafter. Commercially-available herbicidal compounds, i.e., 2,4-D (2,4-dichlorophenoxyacetic acid) and Atrazine served as controls. Untreated plants served as an additional control.

The herbicidal compounds were dissolved in acetone containing an emulsifier combination of Span 85 (sorbitan trioleate) and Tween 80 (polyoxyethylene sorbitan monooleate). The emulsifiers were used at a level such that the finished spray formulations contained 500 ppm Span 85 and 125 ppm Tween 80. The formulations were applied with a Devilbiss atomizer operating at 6 p.s.i. pressure and delivering 50 ml. of formulation on both the pre- and post-emergence tests.

Pre-Emergence Test: Duplicate paper pots, filled with a soil mixture, were seeded at a depth of one-half inch with snap beans, cotton, corn, wheat, mustard, pigweed, crabgrass and foxtail. Immediately after seeding, the soil was sprayed with the formulation. Growth was permitted to occur under artificial light with overhead irrigation. The plants were observed for about 10 days and an injury rating was given in comparison with the untreated controls.

Post-Emergence Test: Duplicate paper pots, filled with vermiculite, were seeded at a depth of one-half inch with the same plants employed in the Pre-Emergence Test. Growth was permitted to occur under artificial light, with irrigation provided by placing the pots in a small amount of water in stainless steel trays. After about ten days when the plants reached a suitable size, they were sprayed with formulation. Observations were made for ten days and an injury rating was given compared with the untreated controls. The injury ratings were made according to the following scales.

| Severity of Injury | | | |
|---|---|---|---|
| 0 | None | 3 | Moderately severe |
| 1 | Slight | 4 | Severe |
| 2 | Moderate | 5 | Death |

| Type of Injury | | | |
|---|---|---|---|
| C | Chlorosis | R | Reduction |
| E | Epinasty | RG | Reduced germination |
| G | General necrosis | S | Stunting |
| H | Hypertrophy | SS | Stem swelling |
| L | Local necrosis | SC | Stem curling |
| M | Mottled | T | Tip burn |
| NF | Nodule formation | TB | Terminal bud |
| NG | No growth | U | Leaf curl upward |
| | | W | Wilting |

Results are shown in the following Table.

TABLE I

HERBICIDAL ACTIVITY OF (METHYLTHIOMETHYL) TRIBUTYLTIN

| Test Plant | Mustard | | Pigweed | | Crabgrass | | Foxtail | | Corn | | Wheat | | Cotton | | Beans | |
|---|---|---|---|---|---|---|---|---|---|---|---|---|---|---|---|---|
| Emergence | Pre | Post | Pre | Post | Pre | Post | Pre | Post | Pre | Post | Pre | Post | Pre | Post | Pre | Post |
| Dosage | | | | | | | | | | | | | | | | |
| One lb/Acre | 0 | 4G | 0 | 2G | 0 | 0 | 0 | 1T | 0 | 1G | 0 | 1G | 0 | 0 | 0 | 0 |
| lb/Acre | 4RG | 5C | 5NG | 5C | 4RG | 4C | 4RG | 4C | 0 | 4C | 0 | 3C | 0 | 5C | 0 | 5C |
| 2,4-D 1 lb/Acre | 4RG | 4E | 4RG | 3E | 0 | 1T | 0 | 0 | 0 | 0 | 0 | 0 | 0 | 2E | 2S | 4E 4SS |
| Atrazine 1 lb/Acre | 2S | 5C | 2S | 4C | 0 | 3C | 0 | 3C | 0 | 0 | 0 | 0 | 0 | 0 | 0 | 3C |
| Untreated | 0 | 0 | 0 | 0 | 0 | 0 | 0 | 0 | 0 | 0 | 0 | 0 | 0 | 0 | 0 | 0 |

From the above data, the pre-emergent selectivity of (methylthiomethyl)tributyltin employed at a dosage of 20 lbs/acre is readily apparent. The control of dicotyledonous (mustard and pigweed) and monocotyledonous (crabgrass and foxtail) weed growth on a pre-emergent basis, while having minimal effect on desirable crops, is evident. Post-emergent activity is also apparent.

The novel compounds of the invention are useful for controlling the growth of undesirable vegetation. As employed herein, the term "undesirable vegetation" refers to any unwanted vegetation including seeds, seedlings and germinated plants. Accordingly, a method aspect of the present invention comprises controlling (i.e., preventing, combating, supressing, inhibiting or eradicating) the growth of weeds and other undesirable vegetation by a method which comprises applying to the area or locus infested with such vegetation a growth-controlling amount of an organotin compound of the invention. Thus, one aspect of the present invention involves the pre-emergent application to earth containing weed seeds a growth-controlling amount of a selective herbicidal compound of the invention. Thus, the growth of a large number of monocotyledenous and dicotyledonous weeds can be inhibited while the growth of the seeds of desirable crops is not adversely affected. This allows a field to be fitted, then planted with corn, wheat, cotton, beans or like crop, and then chemically treated with a compound of the invention with the assurance of a low weed count and at least a normal crop from the seeds.

The post-emergent herbicidal activity of the compounds of the invention can be employed to advantage by the application of such compounds to areas infested with undesirable vegetation. The compounds of the invention can be applied to the foilage of established weed plants or seedlings to effect control or eradication. Thus, the compounds of the invention, when applied to undesirable plant growth, proximate to walkways, gravel roads, power transmission lines, highways, roadways and the like, assure control of such undesirable vegetation.

The compounds of the invention, suitable in effecting desirable control of unwanted vegetation, permit such control without harmful effect on vegetation resulting from subsequent plantings. Thus, the degradability of the organotin compounds of the invention permits substantial control of undesirable vegetation without adverse lingering effect on desirable crops which may be seeded or planted in an area previously treated with a herbicidal compound of the invention.

In accordance with the present invention, undesirable vegetation including weed seeds, seedlings and mature plants, are contacted with the organotin compounds described herein in amounts sufficient to achieve the desired degree of control. The required dosage depends upon many factors such as method of application, pre- or post-emergent treatment, type and quantity of vegetation, the particular organotin compounds employed, the nature of the herbicidal formulation, duration of treatment, climatic conditions, etc. Application rates of from 1 to about 50 pounds of organotin compound per acre are normally satisfactory depending on the factors hereinbefore mentioned. The organotin compounds herein can be applied singly or in combination with each other and/or other materials as more fully described hereinafter.

In actual usage, the organotin herbicides of this invention are applied to undesirably infested areas in the form of herbicidal compositions which comprise a carrier and a growth-controlling amount of one or more of the organotin compounds. Such herbicidal compositions enable the organotin compounds to be applied conveniently to the site of the infestation in any desired quantity. These compositions can be solids, such as dusts, granules or wettable powders or the like, or they can be liquids such as solutions, aerosols, emulsifiable concentrates or the like. The solid compositions generally contain from about 1% to about 95% by weight of the organotin compounds while the liquid compositions generally contain from about 0.5% to about 70% by weight of said compounds.

Suspensions or dispersions of the compounds of the invention in a non-solvent, such as water, are suitably employed in treating plant foliage. Also suitably employed are solutions of the herbicides of the invention in oil which is emulsified in water. Examples of oil solvents include hydrocarbons such as benzene and toluene and halogenated hydrocarbons such as chlorobenzene, chloroform, fluorotrichloromethane and dichlorodifluoromethane.

Aerosols prepared by dissolving compounds of the invention in a highly volatile liquid carrier such as trifluorochloromethane, or by dissolving such compounds in a less volatile solvent, such as benzene, and admixing the resulting solution with a highly volatile liquid aerosol carrier can also be employed to advantage.

Preferred liquid herbicidal compositions for the practice of the invention herein are emulsifiable concentrates which comprise the organotin compound, an emulsifier, and a solvent carrier. Such concentrates can be extended with water and/or oil to any desired concentration of the organotin herbicide for application as sprays to the site of vegetative investation. The emulsifiers used in these concentrates are surface active agents of the anionic, nonionic, cationic, ampholytic or zwitterionic type.

Examples of suitable anionic surface active agents are sodium salts of fatty alcohol sulfates having from 8–18 carbon atoms in the fatty chain and sodium salts of alkyl benzene sulfonates, having from 9 to 15 carbon atoms in the alkyl chain.

Examples of suitable nonionic surface active agents are the polyethylene oxide condensates of alkyl phenols, wherein the alkyl chain contains from about 6 to 12 carbon atoms and the amount of ethylene oxide condensed onto each mole of alkyl phenol is from about 5 to 25 mole.

Suitable cationic surface active agents include dimethyl dialkyl quaternary ammonium salts wherein the alkyl chains contain from about 8 to 18 carbon atoms and the salt forming anion is a halogen.

Suitable ampholytic surface active agents include derivatives of aliphatic secondary or tertiary amines in which one of the aliphatic substituents contains from about 8 to 18 carbon atoms and one contains an anionic water-solubilizing group, e.g., sulfate or sulfo. Specific suitable ampholytic surface active agents are sodium-3-dodecylaminopropionate and sodium-3-dodecyl amino propane sulfonate.

Examples of suitable zwitterionic surface active agents are derivatives of aliphatic quaternary ammonium compounds in which one of the aliphatic constituents contains from about 8 to 18 carbon atoms and one contains an anionic water solubilizing group. Specific examples of zwitterionic surface active agents are 3-(N,N-dimethyl-N-hexadecylammonio) propane-1-sulfonate and 3-(N,N-dimethyl-N-hexadecylammonio)-2-hydroxy propane-1-sulfonate.

Other suitable surface active agents are described in Detergents and Emulsifiers — 1969 Annual by John W. McCutcheon Inc. which is incorporated by reference herein. Suitable solvents for these emulsifiable concentrates include those mentioned hereinbefore.

Suitable dusts can be prepared by admixing the compounds of the invention with dry free-flowing powders such as clay, bentonite, fuller's earth, diatomaceous earth, pyrophyllite, attapulgite, calcium carbonate, chalk or the like. An amount of active compound of up to about 5% is preferred and is suitable for most applications.

The compounds of the present invention are also useful when combined with other herbicides, and/or defoliants, dessicants and the like in the herbicidal compositions heretofore mentioned. These other materials can comprise from about 5% to about 95% of the total active ingredients in the herbicidal compositions.

In addition to effecting control of unwanted vegetation, the method of the present invention has an additional benefit in that the organotin compounds used herein also provide control of insects at the levels used for weed control. The compounds have insecticidal, acaricidal and fungicidal activity as is apparent from the following evaluations.

Insecticidal Evaluation Test: Four insect species as follows were subjected to evaluation tests for insecticidal properties:

I. Adult House Flies
II. Southern Armyworm Larvae
III. Mexican Bean Beetle Larvae
IV. Adult Pea Aphids The test compound, (methylthiomethyl)tributyltin, was dissolved in acetone and dispersed in distilled water with Triton X-100 (iso-octyl phenyl polyethoxy ethanol) emulsifier. The resulting composition was applied for a ten-second period to insects retained in a 2 × 5 inch diameter screened cage. The spray was applied from a Water's vertical spray tower operating at 10 p.s.i. and discharging about 30 ml. of material per minute through an atomizer. The spray descends through an 8 inch stainless steel cylinder to test insects below the atomizer. The insects were retained in the sprayed cages for mortality observations. In the case of House Fly treatment, two-hour data represents knockdown; 24-hour data refers to mortality. The results are set forth in Table II below.

TABLE II

| Conc. (W/V%) | Mortality | | | | |
|---|---|---|---|---|---|
| | House Flies | | Armyworms | Bean Beetles | Aphids |
| | 2 hr. | 24 hr. | 48 hr. | 48 hr. | 48 hr. |
| 0.35 | 32(98) | 20(100) | 100(100) | 100(100) | 100(100) |
| 0.10 | —(100) | —(100) | 40(100) | 30(100) | 75(100) |

Numbers in parentheses refer to control compositions employed in a concentration of active equal to that of the weight/percent volume of the compounds of the invention. In the case of treatment of House Flies, the control compound was 0,0-diethyl 0-(2-iso-propyl,4-methyl-6-pyrimidyl)phosphorothioate; the control for the Southern Armyworm and Mexican Bean Beetle larvae treatments was 1-naphthyl-N-methyl-carbamate; the control for the Pea Aphid treatment was S-[1,2-bis-(ethoxycarbonyl)ethyl]0,0-dimethyl phosphorodithioate.

As can be seen from the foregoing table, (methylthiomethyl)tributyltin has desirable insecticidal properties. Particularly notable are the excellent mortality results in the case of the treatments of Southern Armyworm and Mexican Bean Beetle larvae and Pea Aphids.

Acaricidal Evaluation Test: The Strawberry Spider Mite was employed in tests for acaricidal activity. Bean seedlings were infested with approximately one hundred mites. Dispersions of test compound, (methylthiomethyl)tributyltin, were prepared by dissolving the toxic material in acetone to provide a desired weight/volume percent. The solution was then diluted with water containing Triton X-100 emulsifier, the amount of water being sufficient to provide a stable emulsion. The test suspensions were sprayed on the infested bean seedlings. After five days, the plants were examined both for post-embryonic forms of the mites as well as eggs. The percentage of kill was determined on the basis of the original number of mites subjected to the treatment with the test suspensions. The acaricidal mortality is reported in Table III.

TABLE III

| Strawberry Spider Mite Mortality | |
|---|---|
| %W/V | %Mortality (5 days) |
| 0.35 | 100(100) |
| 0.10 | 95(100) |
| 0.05 | 96(100) |
| 0.01 | 91(84) |
| 0.005 | 11(79) |

As can be seen from the acaricidal data, the compound (methylthiomethyl)tributyltin has desirable acaricidal properties. 4,4'-dichloro-alpha-trichloromethylbenzhydrol results are reported in parentheses in Table III.

The fungicidal activity of (methylthiomethyl)tributyltin of the present invention were evaluated as follows:

The test compound of the invention was dissolved in acetone at levels of 1000, 100 and 10 parts per million. One-half inch filter paper discs were saturated with the test solutions, dried and tested for antifungal activity by the Agar Plate Test, USDA Circular No. 198, 1931. All tests were performed upon Difco Sabouraud Dextrose Agar. All tests were incubated at 25° C., R.H. 96% for five days. Results are reported in Table IV as follows:

TABLE IV

| Test fungus | Width of zone of inhibition(in mm.) | | |
|---|---|---|---|
| | 1000 ppm | 100 ppm | 10 ppm |
| Candida albicans | trace | 0 | 0 |
| Trichophyton mentagrophytes | 3 | trace | 0 |
| Glomerella cingulata | 1 | trace | 0 |
| Sclerotinia fructicola | 3 | 1 | 0 |
| Aspergillus niger | 4 | 1 | trace |
| Chaetomium globosum | 1 | 0 | 0 |

As can be seen from the above data, the compound (methylthiomethyl)tributyltin has fungicidal properties.

What is claimed is:

1. A method of controlling undesirable vegetation which comprises applying to the locus infested with such vegetation a herbicidal amount of a compound having the formula $$R - S - CH_2 - Sn - R_3'$$

where R is selected from the group consisting of alkyl of from 1 to 14 carbon atoms; naphthyl; phenyl; and substituted phenyl; and each R' is alkyl of from 1 to 14 carbon atoms.

2. A method of controlling undesirable vegetation which comprises applying to the locus infested with such vegetation a herbicidal amount of a compound having the formula $$R - S - CH_2 - SN - R_3'$$

wherein R is alkyl of from 1 to 14 carbon atoms, and R' is alkyl of from 1 to 14 carbon atoms.

3. A method of controlling undesirable vegetation which comprises applying to the locus infested with such vegetation a herbicidal amount of a compound having the formula $$R - S - CH_2 - Sn - R_3'$$

wherein R is methyl, and R' is alkyl of from 1 to 14 carbon atoms.

4. The method of claim 3 wherein each R' is butyl.

* * * * *